United States Patent [19]

Kiser

[11] 4,319,057

[45] Mar. 9, 1982

[54] REGENERATION OF MOLECULAR SIEVES

[75] Inventor: Donald L. Kiser, Muscatine, Iowa

[73] Assignee: Grain Processing Corporation, Muscatine, Iowa

[21] Appl. No.: 214,197

[22] Filed: Dec. 8, 1980

[51] Int. Cl.³ .......................... C07C 31/08; B01J 37/00
[52] U.S. Cl. .................................... 568/916; 252/414; 252/455.2; 568/917
[58] Field of Search ................. 568/916, 917; 252/414

[56] References Cited

U.S. PATENT DOCUMENTS

| | | | |
|---|---|---|---|
| 2,457,556 | 12/1948 | Heinemann et al. | 252/414 |
| 2,882,243 | 4/1959 | Milton | 568/917 |
| 2,882,244 | 4/1959 | Milton | 568/917 |
| 3,208,157 | 9/1965 | Stark | 252/414 |
| 3,330,778 | 7/1967 | Irvin | 252/414 |
| 3,347,783 | 10/1967 | Feldbauer, Jr. | |
| 3,398,208 | 8/1968 | Ward | 252/414 |
| 3,422,004 | 1/1969 | Padrta | |
| 3,538,168 | 11/1970 | Mitchell, Jr. | 568/916 |
| 3,691,728 | 9/1972 | Vautrain et al. | |

OTHER PUBLICATIONS

Petroleum vol. 27, col. 6378.
Lowenberg, "J. Applied Chemistry", 9, pp. 417–420, Aug. 1959.

*Primary Examiner*—Joseph E. Evans
*Attorney, Agent, or Firm*—Neuman, Williams, Anderson & Olson

[57] ABSTRACT

Molecular sieves used for dehydration are regenerated with methanol or acetone.

5 Claims, No Drawings

REGENERATION OF MOLECULAR SIEVES

Molecular sieves are used to dehydrate various materials including polar solvents such as, for example, methanol and ethanol, paints and plastics and saturated hydrocarbon streams. Molecular sieves are crystalline zeolites having a basic formula $M_{2/n}O.Al_2O_3.xSiO_2.yH_2O$ where M is a cation of n valence. The conventional means for regenerating the sieves is to desorb the adsorbed water with a stream of hot gas, typically at a temperature of 550° F. This requires considerable energy since the entire system must be heated to a temperature at which water is desorbed. Furthermore, additional energy is required to maintain the system at the elevated temperature for the duration of the desorption cycle, which typically lasts two to four hours.

One object of this invention is to provide a method for regeneration or reactivation without the use of heat of molecular sieves that have been used for dehydration of materials.

Another object of this invention is to provide a method for regeneration of molecular sieves in a manner that permits the molecular sieves to be returned to dehydration service immediately after regeneration.

Another object of the invention is to provide a method for regeneration of molecular sieves with a solvent that can be recovered or dehydrated by distillation.

Another object of the invention is to provide a method for regeneration of molecular sieves by a process which avoids placing stresses on the sieves as results from regenerating procedures utilizing high temperature and cooling cycles.

I have now found that molecular sieves which have been used to dehydrate or remove water from substances can be regenerated with methanol or acetone. Since methanol is a chemical that can be dehydrated by molecular sieves, this finding was totally unexpected. Furthermore, Breck, D. W. and Smith, J. V., "Molecular Sieves", Sci. Amer. 200 85 (1959), state, "The crystals (zeolite molecular sieves) have a particularly strong affinity for water molecules, and will adsorb them in preference to any other substance." Thus, one would expect water to be so strongly held by the molecular sieves that methanol or acetone would not be able to dislodge the bound molecules.

In accordance with this invention, a molecular sieve which has been used for dehydration and which has become spent or which has lost some dehydrating activity because of water absorption is regenerated by contacting the molecular sieve with methanol or acetone. Regeneration efficiency is less with methanol and acetone containing substantial amounts of water and it is thus preferred to employ these regenerating agents in substantially anhydrous condition, i.e, containing not more than about 0.1% by weight water.

The regeneration procedure can be conducted in either a batch or continuous manner. For example, in a typical batch regeneration procedure, spent molecular sieves to be regenerated are placed into a vessel and methanol or acetone preferably containing not more than 0.1% by weight water is brought into contact with the molecular sieves. The amount of methanol or acetone used generally ranges from about at least 2 to 10 milliliters for each gram of the molecular sieves undergoing regeneration. A large ratio of methanol or acetone to the molecular sieve, such as 10 or more to 1, milliliters per gram, is generally preferred to desorb the maximum amount of water. Occasional stirring or other agitation is desirable to improve regeneration efficiency. The methanol or acetone is permitted to remain in contact with the molecular sieves for periods of from about 0.1 to 24 hours. The extent of water desorbed from the molecular sieves increases with extended contact times but with decreasing efficiency. A twenty-four hour contact or equilibration period removes most of the water from the spent molecular sieves, but a four-hour equilibration period usually removes over 90% of the water removed in 24 hours. Thus, from a practical standpoint, a four-hour equilibration or contact period is generally sufficient. After contact with the methanol or acetone for a desired period, the molecular sieves are separated from the bulk of the methanol or acetone by filtration or centrifugation. It is not necessary to treat the regenerated molecular sieves further and they can then be used for dehydration operations, although in some applications it may be desirable to remove residual solvent by methods known to those skilled in the art.

In a typical continuous dehydration operation, including the regeneration step, molecular sieves are packed into a vessel equipped with a bottom distributor plate and inlet and outlet openings at the bottom and top, respectively. The material to be dehydrated is made to flow through the bed until the efficiency of water adsorption by the molecular sieve decreases below a predetermined or acceptable limit. At this point, excess material undergoing dehydration by the sieves is removed therefrom. The sieves are then regenerated or reactivated by slowly pumping or percolating methanol or acetone through the bed. The regeneration efficiency is a function of the flow rate of the methanol or acetone. A relatively slow flow rate increases the contact time of the methanol or acetone with the spent molecular sieves and affords greater moisture removal per unit volume of methanol or acetone. A flow rate which provides at least a 20 minute contact time between the methanol or acetone and the molecular sieves is generally preferred. The moisture exiting from the column containing the sieves can be monitored. The methanol and acetone regeneration operation is continued until the moisture level of the column effluent falls to a low value, such as 0.2% water (weight/volume). After the methanol or acetone remaining in the sieve column is drained therefrom, the molecular sieves are again ready to be used for dehydration purposes.

EXAMPLE I

This example demonstrates the regeneration of spent molecular sieves (Linde Air Products Co. 3A potassium cation) with methanol in a batch regeneration. The molecular sieves had been loaded with water in a humid environment such that the sieves gained 21.5% weight due to moisture adsorption. The hydrated sieves contained 17.7% moisture. Weighed amounts of the sieves were placed in glass-stoppered Erlenmeyer flasks and 100 milliliters of methanol that contained 0.024% water (weight/volume) were added to each flask. The flasks were shaken for up to 24 hours at 25° C. Samples of the supernatant were withdrawn periodically for moisture analysis with the following results:

| Ratio | % of Sieve Water Removed Hours Equilibrated | | | | |
|---|---|---|---|---|---|
| Sieve:Methanol* | 0.5 | 1.0 | 2.0 | 4.0 | 24 |
| 1:12.2 | 34 | 46 | 69 | 76 | 76 |
| 1:6.1 | 29 | 44 | 50 | 56 | 60 |
| 1:3.6 | 28 | 41 | 46 | 47 | 50 |
| 1:2.4 | 33 | 38 | 41 | 41 | 43 |

*Gram (as received weight):Milliliter

EXAMPLE II

The procedures used in Example I were used to determine the effect of temperature on hydrated sieve batch regeneration with methanol. A 1:6.1, gram to milliliters, ratio of sieve to methanol was used at 16° C., 25° C. and 60° C.

| Temperature °C. | % of Sieve Water Removed Hours Equilibrated | | |
|---|---|---|---|
| | 1 | 2 | 4 |
| 16 | 38 | 50 | 54 |
| 25 | 44 | 50 | 56 |
| 60 | 49 | 53 | 68 |

Regeneration efficiency was improved at the elevated temperature. Conducting the regeneration operation at an elevated temperature, such as 60° C., is preferable because of the increased efficiency.

EXAMPLE III

This example demonstrates the regeneration of sieves in a stationary column in a continuous manner. The experimental conditions were as follows:

| | |
|---|---|
| Column dimensions | 0.78 centimeter diameter × 22 centimeters length |
| Temperature | 60° C. |
| Flow rate | 0.4 milliliters per minute |
| Sieve weight | 7.3 grams hydrated (1.3 grams $H_2O$, 6.0 grams as received sieve) |
| Methanol contained | 0.025% $H_2O$ weight/volume |

| Methanol Volume, ml | | Water Removed From Hydrated Sieve | |
|---|---|---|---|
| Aliquot | Accumulative | % of Original | % Accumulative |
| 5 | 5 | 37 | 37 |
| 5 | 10 | 18 | 55 |
| 5 | 15 | 11 | 66 |
| 5 | 20 | 7 | 73 |
| 10 | 30 | 8 | 81 |
| 10 | 40 | 5 | 86 |
| 10 | 50 | 3 | 89 |
| 10 | 60 | 3 | 92 |

EXAMPLE IV

This example shows the effect of temperature when molecular sieves were regenerated in a stationary bed in a continuous manner. The experimental conditions were as follows:

| | |
|---|---|
| Column dimensions | 0.78 centimeter diameter × 33 centimeters length |
| Temperature | as indicated |
| Flow rate | 0.6 milliliters per minute |
| Sieve weight | 12.3-12.4 grams hydrated (1.93 to 1.95 grams $H_2O$) |
| Methanol contained | 0.05% $H_2O$ weight/volume |

| Effluent Volume, ml | | Accumulative Water Removed, % | | | |
|---|---|---|---|---|---|
| Aliquot | Accumulative | 16° C. | 25° C. | 40° C. | 60° C. |
| 5 | 5 | 14 | 14 | 22 | 25 |
| 5 | 10 | 24 | 26 | 37 | 38 |
| 5 | 15 | 31 | 35 | 47 | 48 |
| 5 | 20 | 37 | 42 | 53 | 55 |
| 10 | 30 | 46 | 52 | 64 | 65 |
| 10 | 40 | 53 | 60 | 72 | 72 |
| 10 | 50 | 59 | 67 | 79 | 78 |
| 10 | 60 | 64 | 71 | 84 | 81 |
| 10 | 70 | 68 | 75 | 87 | 84 |
| 10 | 80 | 71 | 78 | 90 | 87 |
| 10 | 90 | 74 | 82 | 93 | 89 |

EXAMPLE V

This example shows the effect of flow rate of the regenerating fluid on efficiency of regeneration of the hydrated molecular sieves. The experimental conditions were as follows:

| | |
|---|---|
| Column dimensions | 0.78 centimeter diameter × 33 centimeters length |
| Temperature | 60° C. |
| Flow rate | As indicated |
| Sieve weight | 12.4-13.9 grams hydrated (1.95-2.30 grams $H_2O$, 10.4-10.7 grams as received sieve) |
| Methanol Contained | 0.02-0.05% $H_2O$ weight/volume |

| Methanol, ml | | Methanol Flow Rate, ml/min | | | | |
|---|---|---|---|---|---|---|
| | | 2 | 1 | 0.8 | 0.6 | 0.4 |
| Aliquot | Accumulative | Accumulative Water Removed, % | | | | |
| 5 | 5 | 18 | 22 | 15 | 25 | 29 |
| 5 | 10 | 29 | 34 | 24 | 38 | 44 |
| 5 | 15 | 37 | 43 | 33 | 48 | 53 |
| 5 | 20 | 43 | 50 | 38 | 55 | 61 |
| 10 | 30 | 54 | 60 | 48 | 65 | 70 |
| 10 | 40 | 60 | 68 | 54 | 72 | 77 |
| 10 | 50 | 65 | 73 | 60 | 78 | 81 |
| 10 | 60 | 69 | 78 | 64 | 81 | 84 |
| 10 | 70 | 73 | 81 | 67 | 84 | 87 |
| 10 | 80 | 76 | 83 | 69 | 87 | 90 |
| 10 | 90 | 79 | 85 | 71 | 89 | |
| 10 | 100 | 81 | 87 | 73 | | |

EXAMPLE VI

The effect of column bed depth and diameter to length ratios on regeneration efficiency was tested. The experimental conditions for these tests were as indicated:

| Column Temperature, °C. | Column Size, cm | | Ratio Diameter: Length | Flow Rate ml/min | Water on Sieve at Start, gms | % Water Removed By No. of Column Volumes | | Total Column Volumes Used | % of Water Removed |
|---|---|---|---|---|---|---|---|---|---|
| | I.D. | Length | | | | 1 | 2 | | |
| 25 | 3.18 | 2.80 | 1:0.9 | 0.32 | 2.94 | 22 | 37 | 6.73 | 67.3 |

| Column Temperature, °C | Column Size, cm I.D. | Column Size, cm Length | Ratio Diameter: Length | Flow Rate ml/min | Water on Sieve at Start, gms | % Water Removed By No. of Column Volumes 1 | % Water Removed By No. of Column Volumes 2 | Total Column Volumes Used | % of Water Removed |
|---|---|---|---|---|---|---|---|---|---|
| 25 | 0.78 | 33 | 1:41 | 0.6 | 2.3 | 32 | 46 | 5.42 | 69 |
| 60 | 0.78 | 22 | 1:28 | 0.4 | 1.28 | 56 | 74 | 6.71 | 92.6 |
| 60 | 0.78 | 33 | 1:41 | 0.4 | 2.3 | 56 | 72 | 4.81 | 90 |
| 60 | 0.78 | 55 | 1:70 | 0.4 | 3.73 | 74 | 91 | 3.80 | 102.4 |
| 60 | 0.78 | 60 | 1:77 | 0.49 | 3.67 | 59 | 75 | 5.22 | 93.7 |
| 60 | 0.78 | 90 | 1:115 | 0.5 | 5.87 | 65 | 79 | 6.26 | 92.3 |

EXAMPLE VII

This example demonstrates the use of molecular sieves to dehydrate ethanol, the regeneration of the sieves and subsequent use of the regenerated sieves to again dehydrate ethanol.

In Test No. 1 ethanol containing 6.12% water (weight/volume) was passed through a bed (175 grams) of molecular sieve (Linde Air Products Co. 3A potassium cation).

In the first dehydration run (Test No. 1) the bed (175 grams) of molecular sieves adsorbed 30.05 grams of water from 1400 milliliters of ethanol. After 1400 milliliters of the aqueous ethanol had been passed through the bed, the molecular sieve bed was regenerated by contacting the bed with 1440 milliliters of methanol containing 0.02% water (weight/volume). The methanol was passed through the sieve bed at a rate of 9.9 milliliters per minute, providing a contact time of 14 minutes. In the regeneration operation 1300 milliliters of the methanol desorbed 21.6 grams of water from the sieves.

After regeneration, Test No. 2 was conducted in which ethanol containing 5.15% water, weight/volume, was passed through the bed of the regenerated sieves. In the second dehydration run (Test No. 2) the bed of sieves adsorbed 22.55 grams of water from 1400 milliliters of ethanol.

The values in the following table are the percentages of water in the ethanol fed to the sieve bed that were found in successive 100 milliliter aliquots of ethanol effluent.

| Ethanol Aliquot, ml | Percent of Water Level in Ethanol Feed Appearing in Effluent Aliquot Test 1 | Percent of Water Level in Ethanol Feed Appearing in Effluent Aliquot Test 2 |
|---|---|---|
| 100 | 0.2 | 14.0 |
| 200 | 0.9 | 20.6 |
| 300 | 11.1 | 35.9 |
| 400 | 30.7 | 45.4 |
| 500 | 51.1 | 56.3 |
| 600 | 65.2 | 67.2 |
| 700 | 76.5 | 77.3 |
| 800 | 85.9 | 81.4 |
| 900 | 91.5 | 87.8 |
| 1000 | 96.7 | 91.3 |
| 1100 | 98.9 | 94.0 |
| 1200 | 105.1 | 94.8 |
| 1300 | 102.5 | 97.5 |
| 1400 | 99.6 | 98.3 |

Following the procedures of this example, a molecular sieve bed is employed to dehydrate ethanol, fusel oil streams, petroleum fractions, organic solvents, purified gases, natural gas, process air streams and the like.

EXAMPLE VIII

This example shows the effect of regenerating hydrated molecular sieves with methanol that is not anhydrous. The following conditions were used in this test:

| | |
|---|---|
| Column dimensions | 0.78 centimeter diameter × 33 centimeters length |
| Temperature | 60° C. |
| Flow rate | 0.4 milliliter per minute |
| Sieve weight | 13.0 grams hydrated (2.3 grams $H_2O$, 10.7 grams "as received" sieve) |

| Regenerant % $H_2O$ in Methanol | % $H_2O$ in Sieve Removed in 1st 20 ml | % $H_2O$ in Sieve Removed in 1st 50 ml | % $H_2O$ in Sieve Removed in 1st 60 ml |
|---|---|---|---|
| 0.02 | 61 | 81 | 84 |
| 1.94 | 49 | 58 | 58 |
| 4.16 | 41 | 48 | 48 |

EXAMPLE IX

A bed of molecular sieves (Linde Air Products Co. 4A sodium cation) which had adsorbed water was regenerated in a continuous manner. The conditions used in this example were as follows:

| | |
|---|---|
| Column dimensions | 0.78 centimeter diameter × 33 centimeters length |
| Temperature | 60° C. |
| Flow rate | 0.5 milliliters per minute |
| Sieve Weight | 12.0 grams hydrated (1.7 grams $H_2O$, 10.3 grams "as received" sieve) |
| Methanol Contained | 0.04% $H_2O$ weight/volume |

| Methanol, ml Aliquot | Methanol, ml Accumulative | % of Water on Sieve Removed Accumulative |
|---|---|---|
| 5 | 5 | 17 |
| 5 | 10 | 34 |
| 5 | 15 | 46 |
| 5 | 20 | 55 |
| 10 | 30 | 66 |
| 10 | 40 | 75 |
| 10 | 50 | 82 |
| 10 | 60 | 86 |
| 10 | 70 | 90 |
| 10 | 80 | 93 |

EXAMPLE X

This example demonstrates the use of acetone to remove water from hydrated sieve in a batch operation.

Hydrated sieve (type 13X, W. R. Grace Co., Davison Division) was prepared by storing 13X in a humid environment. The sieve took on water to the extent that the hydrated sieve contained 17.9% moisture by weight. This hydrated sieve was equilibrated with acetone containing 0.13% weight/volume water.

| Ratio | % of Sieve Water Removed Hours Equilibrated | | | | | |
|---|---|---|---|---|---|---|
| Sieve 13X:Acetone* | 0.5 | 1.0 | 2.0 | 3.0 | 4.0 | 72 |
| 1:12.2 | 24 | 30 | 27 | 33 | 29 | 26 |
| 1:6.1 | 15 | 21 | 20 | 21 | 22 | 21 |

*gram "as received" sieve:milliliters.

EXAMPLE XI

This example demonstrates the removal of water from hydrated sieve using acetone in a column operation. Hydrated sieve (13X, W. R. Grace Co., Davison Division) was packed into a column. Water was removed using an upflow of acetone through the column. The conditions used in this example were as follows:

| | |
|---|---|
| Column dimensions | 0.78 × 38 centimeters |
| Temperature | 50° C. |
| Flow Rate | 0.56 milliliters per minute |
| Sieve Weight | 13.77 grams hydrated (2.46 grams $H_2O$, 11.31 grams "as received" sieve) |
| Acetone contained | 0.37% $H_2O$ weight/volume |

| Milliliter Acetone | | % of Water on Sieve Removed |
|---|---|---|
| Aliquot | Accumulative | Accumulative |
| 5 | 5 | 9 |
| 5 | 10 | 16 |
| 5 | 15 | 22 |
| 5 | 20 | 31 |
| 10 | 30 | 38 |
| 10 | 40 | 39 |
| 10 | 50 | 43 |
| 10 | 60 | 46 |
| 10 | 70 | 48 |
| 10 | 80 | 49 |
| 10 | 90 | 50 |

EXAMPLE XII

This example demonstrates the use of acetone to regenerate a hydrated column of sieve and the subsequent use of that regenerated column for dehydration of ethanol.
Test I refers to the regeneration-with-acetone cycle.
Test II refers to the dehydration-of-ethanol cycle.

| TEST I CONDITIONS | |
|---|---|
| Column dimensions | 0.78 × 38 centimeters |
| Sieve | 13X, hydrated to contain 17.9% water |
| Sieve Weight | 13.48 grams hydrated 13X (2.41 grams $H_2O$, 11.07 grams "as received" sieve) |
| Temperature | 50° C. |
| Acetone Flow Rate | 0.37 milliliters per minute |
| Acetone contained | 0.44% $H_2O$ weight/volume |

| TEST I RESULTS | | |
|---|---|---|
| Milliliter Acetone | | % of Water on Sieve Removed |
| Aliquot | Accumulative | Accumulative |
| 5 | 5 | 13 |
| 5 | 10 | 36 |
| 5 | 15 | 44 |
| 5 | 20 | 50 |
| 10 | 30 | 64 |
| 10 | 40 | 70 |
| 10 | 50 | 73 |
| 10 | 60 | 74 |
| 10 | 70 | 75 |
| 10 | 80 | 77 |
| 10 | 90 | 78 |

The column was air-purged at the end of Test I.

| TEST II CONDITIONS | |
|---|---|
| Temperature | 50° C. |
| Ethanol Flow Rate | 0.4 milliliters per minute |
| Ethanol contained | 6.14% $H_2O$ weight/volume |

| TEST II RESULTS | | |
|---|---|---|
| Milliliter Ethanol | | % of Water in Feed Appearing in Effluent |
| Aliquot | Accumulative | Accumulative |
| 5 | 5 | 33 |
| 5 | 10 | 35 |
| 5 | 15 | 40 |
| 5 | 20 | 47 |
| 10 | 30 | 61 |
| 10 | 40 | 70 |
| 10 | 50 | 76 |

The advantage of the present invention include, among others: (1) the adsorptive capacity of molecular sieves can be restored to high levels in a convenient manner; (2) conventional apparatus can be used for regenerating the sieves in accordance with the invention; and (3) no preliminary treatment of the molecular sieves is required before processing.

Those modifications and equivalents which fall within the spirit of the invention are to be considered a part thereof.

What is claimed is:

1. A process for regenerating crystalline zeolitic molecular sieves containing adsorbed water which comprises contacting the molecular sieves with methanol or acetone.

2. A process in accordance with claim 1 wherein the methanol or acetone is substantially anhydrous methanol or substantially anhydrous acetone.

3. A process in accordance with claim 1 wherein contact of the molecular sieves with methanol or acetone is carried out at an elevated temperature.

4. A process for removing water from water-containing ethanol which comprises passing the water-containing ethanol through a bed of molecular sieves until the water adsorbing capacity of the molecular sieve bed falls to a predetermined level, then passing methanol or acetone through said molecular sieve bed to restore the water adsorbing capacity, and then again passing water-containing ethanol through said molecular sieve bed.

5. A process according to claim 4 wherein the methanol or acetone employed is substantially anhydrous methanol or substantially anhydrous acetone.

* * * * *

UNITED STATES PATENT AND TRADEMARK OFFICE
CERTIFICATE OF CORRECTION

PATENT NO. : 4,319,057
DATED : March 9, 1982
INVENTOR(S) : Donald L. Kiser

It is certified that error appears in the above-identified patent and that said Letters Patent are hereby corrected as shown below:

Column 6, line 29, insert as the first line of the heading over columns 2 through 4 of the table, -- Regeneration Efficiency -- line 31, insert between the third and fourth lines of the heading over column 1 of the table, -- Weight/Volume --

Signed and Sealed this

Eighteenth Day of May 1982

[SEAL]

Attest:

GERALD J. MOSSINGHOFF

Attesting Officer

Commissioner of Patents and Trademarks